US006613709B1

(12) United States Patent
Merlen et al.

(10) Patent No.: US 6,613,709 B1
(45) Date of Patent: Sep. 2, 2003

(54) CATALYST COMPRISING AT LEAST ONE ZEOLITE WITH STRUCTURE TYPE NES AND RHENIUM, AND ITS USE FOR TRANSALKYLATION OF ALKYLAROMATIC HYDROCARBONS

(75) Inventors: Elisabeth Merlen, Rueil-Malmaison (FR); Fabio Alario, Neuilly sur Seine (FR); Nathalie Ferrer, Montesson (FR); Olivia Martin, Nanterre (FR)

(73) Assignee: Institut Francais du Petrole, Cedex (FR)

( * ) Notice: Subject to any disclaimer, the term of this patent is extended or adjusted under 35 U.S.C. 154(b) by 1 day.

(21) Appl. No.: 09/642,020

(22) Filed: Aug. 21, 2000

(30) Foreign Application Priority Data

Aug. 19, 1999 (FR) ............................................. 99 10652

(51) Int. Cl.[7] ................................................ B01J 29/06
(52) U.S. Cl. ............................. 502/64; 502/66; 502/74
(58) Field of Search ............................... 502/64, 66, 74

(56) References Cited

U.S. PATENT DOCUMENTS

| 4,983,273 | A | * | 1/1991 | Kennedy et al. | .......... 208/111.3 |
| 5,254,787 | A | | 10/1993 | Dessau | .................. 585/654 |
| 5,345,021 | A | * | 9/1994 | Casci et al. | .................. 585/467 |
| 5,990,371 | A | * | 11/1999 | Martens et al. | ................ 502/61 |
| 6,036,846 | A | * | 3/2000 | Benazzi et al. | .......... 208/111.3 |
| 6,106,698 | A | * | 8/2000 | Benazzi et al. | .............. 208/109 |
| 6,111,158 | A | * | 8/2000 | Marinangeli et al. | ........ 585/455 |
| 6,123,831 | A | * | 9/2000 | Benazzi et al. | .............. 208/109 |
| 6,126,912 | A | * | 10/2000 | Bourges et al. | .............. 423/235 |
| 6,149,799 | A | * | 11/2000 | Raybaud et al. | ............. 208/108 |
| 6,198,015 | B1 | * | 3/2001 | Marcilly et al. | ............... 502/61 |

FOREIGN PATENT DOCUMENTS

| EP | 0 825 151 A1 | 2/1998 |
| EP | 0 925 822 A1 | 6/1999 |
| FR | 2 765 237 | 12/1998 |

* cited by examiner

*Primary Examiner*—Tom Dunn
*Assistant Examiner*—Christina Ildebrando
(74) *Attorney, Agent, or Firm*—Millen, White, Zelano, Branigan, P.C.

(57) ABSTRACT

The present invention concerns a catalyst which contain at least one zeolite with structure type NES, preferably NU-87, comprising silicon and at least one element T selected from the group formed by aluminium, iron, gallium and boron. Preferably, element T has been extracted so that the overall Si/T atomic ratio is more than 20. This zeolite is at least partially in its acid form. The binder is preferably alumina. The catalyst also contains at least one metal selected from the group formed by group VIIB, group VIB and iridium, preferably rhenium. Finally, the catalyst optionally also contains at least one metal selected from the group formed by elements from groups III and IV of the periodic table, preferably indium or tin. The present invention also concerns the use of the catalyst in a process for transalkylating alkylaromatic hydrocarbons such as toluene and alkylaromatic compounds containing at least 9 carbon atoms. In particular, this catalyst is highly effective in treating C9+ aromatic feeds containing more than 5% by weight of aromatic olefins containing 10 carbon atoms and more, this feed possibly also containing benzene.

26 Claims, No Drawings

CATALYST COMPRISING AT LEAST ONE ZEOLITE WITH STRUCTURE TYPE NES AND RHENIUM, AND ITS USE FOR TRANSALKYLATION OF ALKYLAROMATIC HYDROCARBONS

FIELD OF THE INVENTION

The present invention relates to a catalyst which can, for example, be used in aromatic hydrocarbon transformation reactions. More precisely, it concerns a catalyst for alkylaromatic hydrocarbon transalkylation, preferably transalkylation of toluene and aromatic compounds containing at least 9 carbon atoms, to produce xylenes. The present invention also relates to the preparation of said catalyst and to its use in an alkylaromatic hydrocarbon transalkylation process.

PRIOR ART

A number of catalysts for dismutation and/or transalkylation have already been described in the prior art, and are based on mordenite (United States patents U.S. Pat. No. 3,506,731, U.S. Pat. No. 4,151,120, U.S. Pat. No. 4,180,693, U.S. Pat. No. 4,210,770, U.S. Pat. No. 3,281,483, U.S. Pat. No. 3,780,121 and U.S. Pat. No. 3,629,351) or based on omega zeolite (U.S. Pat. No. 5,210,356, U.S. Pat. No. 5,371,311).

European patent EP-B1-0 378 916 describes NU-87 zeolite, a zeolite with structure type NES, and a method for its preparation in the presence of a salt of a polymethylene diammonium cation, for example decamethonium bromide. In that patent, rhenium is cited among numerous other elements for its hydrodehydrogenating properties.

U.S. Pat. No. 5,641,393 concerns SSZ-37 zeolite with a $SiO_2/Al_2O_3$ ratio for the as synthesised zeolite of more than 400. The synthesis of that zeolite is different from that of NU-87 in that the template is the N,N-dimethyl-4-azoniatricyclo[5.2.2.0$^{(2\cdot 6)}$]undec-8-ene for the SSZ-37 zeolite. The importance of NU-87 zeolite with structure type NES for dismutation and/or transalkylation of alkylaromatic hydrocarbons has been demonstrated in the Applicant's French patent FR-A-2 752 568. That patent also mentions the importance of adding a metal such as nickel.

In EP-A1-0 731 071, the use of a catalyst based on mordenite zeolite and rhenium is described for transalkylation of aromatic C9 cuts comprising an aromatic compound containing at least one ethyl group. While rhenium is the preferred metal, other metals (Ni, Co, Mo, Cr and W) are cited as being suitable.

SUMMARY OF THE INVENTION

The catalyst of the present invention contains at least one zeolite with structure type NES, preferably NU-87, comprising silicon and at least one element T selected from the group formed by aluminium, iron, gallium and boron. Preferably, element T has been extracted so that the overall atomic ratio Si/T is more than 20. This zeolite is at least partially in its acid form. The binder is preferably alumina. The catalyst also contains at least one metal selected from the group formed by group VIIB and group VIB from the periodic table and iridium, preferably rhenium. Finally, the catalyst optionally also contains at least one metal selected from the group formed by elements from groups III and IVA of the periodic table, preferably indium or tin. The present invention also concerns the use of the catalyst in a process for transalkylating alkylaromatic hydrocarbons such as toluene and alkylaromatic compounds containing at least 9 carbon atoms. In particular, this catalyst is highly effective in treating C9+ aromatic feeds containing more than 5% by weight of aromatic olefins containing 10 carbon atoms and more, this feed possibly also containing benzene.

IMPORTANCE OF THE INVENTION

It has been discovered that a catalyst containing at least one zeolite with structure type NES, preferably NU-87 zeolite, preferably dealuminated so as to obtain a Si/T ratio of more than about 20, at least partially and preferably practically completely in its acid form, and at least one metal selected from the group formed by metals from groups VIIB, VIB and iridium, preferably rhenium, leads to catalytic performances, in particular activities, stabilities and selectivities, which are improved for transalkylation reactions of alkylaromatic hydrocarbons such as toluene and alkylaromatic compounds containing at least 9 carbon atoms with respect to prior art catalysts. In particular, this catalyst is very effective in treating C9+ aromatic feeds containing a high percentage of aromatic molecules containing 10 carbon atoms and more (over 5% by weight), meaning that these heavy molecules (such as dimethylethylbenzenes, diethylbenzenes . . . ) can be upgraded to xylenes, with selectivities and stabilities which are improved over the prior art, and also producing benzene with an improved purity.

DESCRIPTION OF THE INVENTION

The invention thus concerns a catalyst containing at least one zeolite with structure type NES, preferably a NU-87 zeolite, in an amount of 30% to 90%, preferably 60% to 85% by weight, and at least one matrix (or binder) making up the complement of the catalyst to 100%. In a preferred embodiment, said zeolite, preferably NU-87, comprising silicon and at least one element T selected from the group formed by aluminium, iron, gallium and boron, preferably aluminium, is dealuminated and at least partially, preferably practically completely in its acid form. The overall Si/T atomic ratio of said zeolite, when it is dealuminated, is generally over 20, preferably over 25, more preferably in the range about 25 to about 350, still more preferably in the range 25 to 250, or yet still more preferably in the range about 25 to about 150. When it is included in the catalyst of the invention, the zeolite with structure type NES is at least partially, preferably practically completely in its acid form, i.e., in its hydrogen form ($H^+$). The sodium content is less than 0.1% by weight, preferably less than 0.05% by weight with respect to the total weight of dry zeolite.

Said catalyst also comprises at least one metal selected from the group formed by metals from groups VIIB, VIB and iridium, preferably rhenium, in an amount in the range 0.01% to 5%, preferably in the range 0.05% to 3% by weight, and optionally at least one element selected from the group formed by groups IIIA and IVA of the periodic table, preferably selected from the group formed by indium and tin in an amount in the range 0.01% to 5%, preferably in the range 0.5% to 3% by weight. Highly preferably, iridium is the only group VIII element which may be is included in the catalyst of the invention.

The matrix, present in an amount in the range 10% to 60% , preferably in the range 15% to 40% by weight with respect to the total catalyst weight, is generally selected from the group formed by clays (for example natural clays such as kaolin or bentonite), magnesia, aluminas, silicas, titanium oxide, boron oxide, zirconia, aluminium phosphates, titanium phosphates, zirconium phosphates, silica-aluminas and charcoal, preferably selected from the group formed by aluminas and clays, more preferably from aluminas.

The present invention also concerns the preparation of the catalyst.

The NES zeolite included in the catalyst of the present invention is preferably NU-87 zeolite prepared in accordance with EP-B1-0 378 916. Thus the NU-87 zeolite is prepared by mixing a source of silicon and a source of an element T, an alkali cation and an organic template selected from salts of polymethylene diammonium cations, for example decamethonium bromide. The NES zeolite used in the catalyst of the present is preferably such that the element T has been extracted from the framework.

In order to prepare the dealuminated NU-87 zeolite with structure type NES of the invention, in the preferred case where element T is aluminium, two dealumination methods can be used starting from an as synthesised zeolite with structure type NES comprising an organic template. They are described below. However, any other method which is known to the skilled person can also be used in the invention.

These methods described for aluminium can also be suitable for other elements T.

The first method, direct acid attack, comprises a first calcining step carried out in dry air, at a temperature which is generally in the range 450° C. to 550° C., which eliminates the organic template present in the micropores of the zeolite, followed by a step in which the zeolite is treated with an aqueous solution of a mineral acid such as $HNO_3$ or HCl or an organic acid such as $CH_3CO_2H$. This latter step can be repeated as many times as is necessary to obtain the desired degree of dealumination. Between these two steps (calcining in air and direct acid attack), one or more ion exchange steps can be carried out using at least one $NH_4NO_3$ solution, to at least partially and preferably almost completely eliminate the alkaline cation, in particular sodium. Similarly, at the end of the direct acid attack dealumination step, one or more ion exchange steps may be carried out using at least one $NH_4NO_3$ solution to eliminate residual alkaline cations, in particular sodium.

In order to obtain the desired Si/Al ratio, the operating conditions must be correctly selected; the most critical parameters in this respect are the temperature of the treatment with the aqueous acid solution, the concentration of the latter, its nature, the ratio between the quantity of acid solution and the mass of the treated zeolite, the treatment period and the number of treatments carried out.

Dealumination can also be accomplished using chemical dealuminating agents such as (by way of non-limiting examples) silicon tetrachloride ($SiCl_4$), ammonium hexafluorosilicate [$(NH_4)_2SiF_6$], and ethylenediaminetetra-acetic acid (EDTA), including its mono and disodium forms. These reactants can be used in solution or in the gaseous phase, for example in the case of $SiCl_4$.

The second dealumination method, heat treatment (in particular using steam, by steaming) followed by acid attack, comprises firstly calcining in dry air at a temperature which is generally in the range 450° C. to 550° C., to eliminate the organic structuring agent occluded in the micropores of the zeolite. The solid obtained then undergoes one or more ion exchanges using at least one $NH_4NO_3$ solution, to eliminate at least a portion, preferably practically all, of the alkaline cation, in particular sodium, present in the cationic position of the zeolite. The zeolite obtained then undergoes at least one framework dealumination cycle comprising at least one heat treatment which is optionally and preferably carried out in the presence of steam, at a temperature which is generally in the range 500° C. to 900° C., and optionally followed by at least one acid attack using an aqueous solution of a mineral or organic acid as defined above. The conditions for calcining in the presence of steam (temperature, steam pressure and treatment period), also the post-calcining acid attack conditions (attack period, concentration of acid, nature of acid used and the ratio between the volume of the acid and the mass of zeolite) are adapted so as to obtain the desired level of dealumination. For the same reason, the number of heat treatment—acid attack cycles can be varied.

In a variation of this second method, the acid attack step, i.e., treatment using a solution of an acid, can be replaced by treatment with a solution of a chemical dealuminating compound such as those cited above, for example, namely silicon tetrachloride ($SiCl_4$), ammonium hexafluorosilicate [$(NH_4)_2SiF_6$], ethylenediaminetetra-acetic acid (EDTA), including its mono and disodium forms.

In the preferred case when T is aluminium, the framework dealumination cycle, comprising at least one heat treatment step, optionally and preferably carried out in the presence of steam, and at least one attack step carried out on the zeolite with structure type NES in an acid medium, can be repeated as often as is necessary to obtain the dealuminated NU-87 zeolite having the desired characteristics. Similarly, following the heat treatment, optionally and preferably carried out in the presence of steam, a number of successive acid attacks can be carried out using different acid concentrations.

A variation of this second dealumination method comprises heat treating the zeolite with structure type NES containing the template, at a temperature generally in the range 550° C. to 900° C., optionally and preferably in the presence of steam. In this case, the steps of calcining the template and dealumination of the framework by heat treatment are carried out simultaneously. Then the zeolite is optionally treated with at least one aqueous solution of a mineral acid (for example $HNO_3$ or HCl) or an organic acid (for example $CH_3CO_2H$) finally, the solid obtained can optionally undergo at least one ion exchange with at least one $NH_4NO_3$ solution to eliminate practically all of the alkali cation, in particular sodium present in the cationic position in the zeolite.

In a preferred implementation of the invention, a dealumination method is used which leads to a reduction in the number of aluminium atoms in the major portion of the zeolite grain and not solely on the surface of the grains. Preferred dealuminated NES zeolites comprise a mesoporous network in the zeolite grain which can be seen using a transmission electron microscope.

The catalyst can be prepared using any method which is known to the skilled person. In general, it is obtained by mixing the matrix and the zeolite then forming. The element selected from the group formed by elements from groups VIIB, VIB and iridium can be introduced either before forming, of during mixing, or, as is preferable, after forming. It is thus understood that the matrix+zeolite mixture is a support for the catalyst containing the element selected from the group formed by elements from groups VIIB, VIB and iridium. Forming is generally followed by calcining, generally at a temperature in the range 250° C. to 600° C. The element from the group formed by group VIIB, group VIB and iridium can be introduced after said calcining step. In all cases, said element is generally chosen to be deposited either practically completely on the zeolite, or practically completely on the matrix, or partly on the zeolite and partly on the matrix, this choice being made in a manner which is known to the skilled person by manipulating the parameters used during said deposition, such as the nature of the precursor selected to carry out said deposition.

The element from the group formed by group VIIB, group VIB and iridium, preferably rhenium, can thus be deposited on the zeolite-matrix mixture which has already been formed using any method which is known in the art. Such deposition is generally accomplished by dry impregnation, ion exchange(s) or co-precipitation. Non-limiting examples of such precursors which can be cited are perrhenic acid and ammonium perrhenate, deposited by dry impregnation, for example.

Deposition of the element from the group formed by elements from groups VIIB, VIB and iridium is generally followed by calcining in air or in oxygen, generally in the range 300° C. to 600° C., preferably in the range 350° C. to 550° C., for a period in the range 0.5 to 10 hours, preferably in the range 1 to 4 hours.

When the catalyst contains a plurality of metals, the metals can all be introduced in the same manner or using different techniques, before or after forming and in any order. When the technique used is ion exchange, several successive exchange steps may be necessary to introduce the required quantities of metals.

The catalyst of the invention is generally formed into pellets, aggregates, extrudates or beads, depending on its use, preferably in the form of extrudates or beads.

As an example, one preferred method for preparing the catalyst of the invention consists of mixing the zeolite in a moist gel of matrix (generally obtained by mixing at least one acid and a powdered matrix), for example alumina, for the period necessary to obtain good homogeneity of the paste produced, namely for about ten minutes, for example, then passing the paste through a die to form extrudates, for example with a diameter in the range 0.4 mm to 4 mm. After oven drying for several minutes at 100° C. then calcining, for example for two hours at 400° C., at least one element, for example rhenium, can be deposited, for example dry impregnating an ammonium perrhenate solution, deposition being followed by final calcining, for example for two hours at 400° C. Preferably, the catalyst obtained is characterized by a macroscopic metal distribution coefficient, obtained from its profile determined using a Castaing microprobe, defined as the ratio of the concentrations of said metal in the core of the grain with respect to the edge of the same grain, preferably in the range 0.7 to 1.3, limits included. Further, and preferably, the catalyst of the present invention in the form of beads or extrudates has a bed crush strength, determined using the Shell method (SMS 1471–74), of more than 0.7 MPa.

Preparation of the catalyst generally ends with final calcining, normally at a temperature which is in the range 250° C. to 600° C., preferably preceded by drying, for example oven drying, at a temperature which is in the range from ambient temperature to 250° C., preferably 40° C. to 200° C. The drying step is preferably carried out during the temperature rise required to carry out calcining.

Reduction in hydrogen can then be carried out, generally at a temperature in the range 300° C. to 600° C., preferably in the range 350° C. to 550° C., for a period in the range 1 to 10 hours, preferably in the range 2 to 5 hours. Such a reduction can take place ex situ or in situ, with respect to the location where said catalyst is used in a given reaction.

The catalyst of the invention can optionally contain sulphur. In this case, the sulphur is introduced into the formed and calcined catalyst containing the element(s) cited above, either in situ before the catalytic reaction, or ex situ. Sulphurisation is carried out using any sulphurising agent which is known to the skilled person, such as dimethyl disulphide or hydrogen sulphide. Sulphurisation can optionally take place after reduction. With in situ sulphurisation, reduction takes place before sulphurisation if it has not already been reduced. With ex situ sulphurisation, reduction then sulphurisation is carried out.

The catalyst containing the zeolite of the invention, in particular NU-87, is used to convert hydrocarbons.

In particular, the invention concerns the use of said catalyst in transalkylating alkylaromatic hydrocarbons, preferably transalkylating toluene and alkylaromatic hydrocarbons, generally C9+ (i.e., containing at least 9 carbon atoms per molecule), with toluene-AC9+ mixtures (where AC9+ designates alkylaromatic hydrocarbons containing at least 9 carbon atoms per molecule) which can contain 0 to 100% of AC9+ with respect to the total mixture. Said catalyst has been proved to be highly effective for this use, as it is particularly active, selective and stable even in the presence of feeds to be treated containing a large quantity of heavy aromatic compounds AC9+, these heavy aromatic compounds possibly containing a large proportion of AC 10+. Thus AC9+ feeds containing at least 5% and up to 25% by weight or even more of AC10+ can be upgraded. Non limiting examples which can be cited are dimethylethylbenzenes, diethylbenzenes, propylethylbenzenes . . . . The use of this catalyst for transalkylating heavy alkylaromatic compounds is thus of particular interest.

The operating conditions for said use are generally as follows: a temperature in the range 250° C. to 650° C., preferably in the range 350° C. to 550° C.; a pressure in the range 1 to 6 MPa preferably in the range 2 to 4.5 MPa; an hourly space velocity, expressed in kilograms of feed introduced per kilogram of catalyst per hour, in the range 0.1 to 10 $h^{-1}$, preferably in the range 0.5 to 4 $h^{-1}$, a mole ratio of hydrogen to hydrocarbons in the range 2 to 20, preferably in the range 3 to 12 mol/mol.

EXAMPLES

Example 1

Preparation of a Catalyst Based on Mordenite and Rhenium, not in Accordance with the Invention The starting material used was a mordenite zeolite with an overall Si/Al atomic ratio of 7.6, and a sodium content of about 3.8% with respect to the weight of dry mordenite zeolite.

This mordenite zeolite underwent acid attack, using an 8N solution of nitric acid at about 100° C. for 4 hours to partially extract the aluminium atoms present in the zeolitic framework of the mordenite. The dealuminated mordenite zeolite then underwent ion exchange in a 10N $NH_4NO_3$ solution at about 100° C. for 4 hours to remove the residual sodium.

At the end of these treatments, the mordenite zeolite in its H form had an overall Si/Al atomic ratio of 47.9 and a sodium content of 48 ppm with respect to the weight of dry mordenite zeolite.

This zeolite was then formed by extrusion with an alumina gel to obtain, after drying and calcining in dry air, a support S1 which contain 80% by weight of mordenite zeolite in its H form and 20% of alumina.

Support S1 was then impregnated using an aqueous solution of perrhenic acid, so as to deposit 0.3% by weight of rhenium on the solid. The moist solid was then dried at 120° C. for 12 hours and calcined in a stream of dry air at a temperature of 500° C. for one hour. The catalyst C1 obtained contained 79.7% of mordenite, 20.0% of alumina and 0.29% of rhenium.

Example 2

Preparation of a Catalyst Based on NU-87 and Nickel, not in Accordance with the Invention

The starting material used was a NU-87 zeolite with an overall Si/Al atomic ratio of 17.2, and a sodium content corresponding to an Na/Al atomic ratio of 0.144. This NU-87 zeolite had been synthesised in accordance with European patent application EP-A-0 377 291 or EP-B-0 378 916.

This NU-87 zeolite first underwent dry calcining at 550° C. in a stream of air and nitrogen for 6 hours. The solid obtained then underwent ion exchange in a 10N $NH_4NO_3$ solution at about 100° C. for 4 hours. The NU-87 zeolite then underwent a treatment with a 7N nitric acid solution at about 100° C. for 5 hours. The volume V of the solution of nitric acid used (in ml) was equal to 10 times the weight W of the dry NU-87 zeolite (V/W=10). This treatment using a 7N nitric acid solution was repeated a second time under the same operating conditions.

At the end of these treatments, the zeolite obtained was in its H form and had an overall Si/Al atomic ratio of 34.6 and a Na/Al ratio of 0.007.

The H-NU-87 zeolite was then formed by extrusion with an alumina gel to obtain, after drying and calcining in dry air, a support S2 which contained 70% by weight of H-NU-87 zeolite and 30% of alumina.

Support S2 was then dry impregnated using a nickel nitrate solution to deposit 0.6% by weight of nickel on the catalyst. The moist solid was then dried at 120° C. for 12 hours and calcined in a stream of dry air at 500° C. for one hour. Catalyst C2 obtained contained 69.6% by weight of NU-87 in its H form, 29.8% of alumina and 0.58% of nickel.

Example 3

Preparation of a Catalyst Based on NU-87 and Rhenium, in Accordance with the Invention

Support S2 was impregnated using an aqueous solution of ammonium perrhenate, so as to deposit 0.3% by weight of rhenium on the solid. The moist solid was then dried at 120° C. for 12 hours and calcined in a stream of dry air at 500° C. for one hour. Catalyst C3 obtained contained 69.8% of NU-87 in its hydrogen form, 29.9% of alumina and 0.31% of rhenium.

Example 4

Comparison of Catalytic Performances of Catalysts C1 and C2, not in Accordance with the Invention, and Catalyst C3, in Accordance with the Invention

The catalysts were first reduced in hydrogen at 450° C. for 2 hours.

Catalyst C2 was then treated with a feed containing dimethyl disulphide (DMDS) in a concentration such that the sulphur/metal atomic ratio was 1.5. This treatment was carried out for 3 hours at 400° C., maintaining a hydrogen/hydrocarbon ratio of 4.

The catalytic tests were carried out under the following operating conditions:

Temperature: 400° C.;
Total pressure: 30 bg
$H_2$/HC: 5 mol/mol.
Two types of feed were used:
a feed A1 essentially constituted by aromatic compounds containing 9 carbon atoms, containing 4.3% by weight of aromatic compounds containing 10 carbon atoms;
a feed AC9+, A2, containing 17.0% by weight of aromatic compounds containing 10 carbon atoms.

1 Comparison of Catalysts Based on NU-87:

The two catalysts based on NU-87, one containing nickel (C2, not in accordance with the invention) and the other containing rhenium (C3, in accordance with the invention) were firstly compared under the same conditions with a feed containing 50% of toluene and 50% of feed A1. The results are shown in Table 1:

TABLE 1

|  | C2 (not in accordance with the invention) | C3 (in accordance with the invention) |
| --- | --- | --- |
| Overall conversion (%) | 51.9 | 52.8 |
| Yields (weight %) |  |  |
| Light compounds ($C_1$–$C_4$) | 3.4 | 9.8 |
| Benzene + xylenes | 41.8 | 42.8 |
| Ethylbenzene | 2.0 | 0.4 |
| Heavy compounds | 5.1 | 1.9 |
| Ethyltoluene | 3.6 | 0.6 |
| Dimethylethylbenzene | 1.6 | 0.2 |

The performance of the catalyst of the invention based on rhenium was substantially improved over that of the nickel-based catalyst (prior art). In fact, it was particularly active with a higher overall conversion for half as much metal. Further, the benzene+xylene yield increased and the low ethylbenzene yield facilitated para-xylene separation. Finally, the yield of light compounds increased to the detriment of the heavy compound yield, which favoured the stability of the catalyst. This increase in the $C_1$–$C_4$ light fraction was essentially due to the dealkylating properties of this novel catalyst. The results of Table 1 show that catalyst C3, in accordance with the invention, dealkylated ethylbenzene leading to the formation of $C_2$ molecules. A detailed analysis of the aromatic compounds containing 8, 9 and 10 carbon atoms present in the feed and containing at least one alkyl group containing 2 carbon atoms or more showed strong dealkylation of all of these compounds with catalyst C3, leading to a high yield of light compounds.

The stability of catalyst C3, in accordance with the invention, was also improved over catalyst C2, which was not in accordance with the invention. In the case of nickel-based catalyst C2, in a feed of 50% of toluene/50% A1, the overall conversion fell from 51.9% to 46.5% in 260 hours, corresponding to a deactivation of 3.8% over 100 hours. In the case of rhenium-based catalyst C3, the deactivation was 3.6% over 100 hours for a much heavier feed (20% T/80% A2) with an overall drop in conversion from 53.5% to 51.6%. The skilled person is well aware that stability falls when the average molecular weight of the feed increases. The catalyst of the invention thus surprisingly has a substantially improved stability. This shows that the rhenium-based catalyst is much more stable than the nickel-based catalyst.

2. Comparison of Catalysts Containing Rhenium:

The two catalysts containing rhenium, one based on MOR zeolite (C1, not in accordance with the invention) and the other based on NU-87 zeolite (C3, in accordance with the invention), were compared at iso-conversion with a feed containing 20% of toluene and 80% of feed A2. The results are shown in Table 2:

TABLE 2

|  | 20% toluene/80% A2 | |
| --- | --- | --- |
| Feed Catalysts | C1 (not in accordance with the invention) | C3 (in accordance with the invention) |
| Overall conversion (%) | 53.0 | 52.8 |
| Yields (weight %) | | |
| Light, C1–C4 | 12.5 | 11.8 |
| C5+ | 0.8 | 0.3 |
| Benzene | 5.8 | 5.5 |
| Xylenes | 33.3 | 34.4 |
| Ethylbenzene | 0.7 | 0.5 |
| Heavy compounds | 0.8 | 1.1 |
| Ethyltoluene | 1.7 | 1.1 |
| Dimethylethylbenzene | 0.9 | 0.7 |

These results demonstrate the better selectivity of the catalyst based on NU-87. The xylene yield was increased while the yield of $C_5^+$ compounds, which are secondary and undesirable side products of the reaction, was substantially reduced. Certain of the compounds of this $C_5^+$ fraction deleteriously affect the purity of the benzene produced. The purity of distilled benzene can be estimated (in accordance with International patent application WO-A-98/56741) using the following formula:

Purity of distilled benzene=$100*Bz/(Bz+a+b+c+d)$

Where a=$0.1*C_6$ paraffins,
b=$0.7*$methylcyclopentane,
c=cyclohexane;
d=$C_7$ naphthenes.

In the case of catalyst C1, not in accordance with the invention, the estimated benzene purity was 98.17% while in the case of catalyst C3, in accordance with the invention, this estimated purity was 99.69%. This very substantial increase is a supplemental advantage during the use of the catalyst of the invention.

Further, this $C_5$ fraction essentially contains paraffins containing 5 or 6 carbon atoms which originate from aromatic rings (opening and cracking). Thus the loss of aromatic nuclei increases, and as a result there is a loss of desired products in the case of catalyst C1, not in accordance with the invention.

A detailed analysis of aromatic compounds containing 9 and 10 carbon atoms containing ethyl groups shown in Table 2 shows that the dealkylating properties of the catalyst of the invention based on NU-87 are superior to those of the mordenite-based catalyst not in accordance with the invention. As an example, the conversion of ethyltoluene present in an amount of 24.25% in the feed is 95.4% with C3 as opposed to 92.9% with C1. However, it can be seen that catalyst C1 leads to a higher yield of $C_1$–$C_4$ fraction. In fact, two types of reactions produce these light compounds: dealkylation of alkylaromatic compounds where the alkyl groups contain two carbon atoms or more and ring opening reactions followed by cracking. The mordenite-based catalyst thus leads to more cracking and less dealkylation than the NU-87 based catalyst which thus performs better for the dealkylation reaction to upgrade heavy alkylaromatic compounds comprising ethyl, propyl etc groups to (polymethyl) benzenes which can be upgraded to xylenes.

These different examples demonstrate the importance of this novel catalyst and its use for transalkylation in the presence of large quantities of AC9 and large quantities of AC9 and AC 10. It is more active for conversion of heavy molecules by selective dealkylation and leads to an improved yield of xylenes and leads to an improved benzene purity. This conversion of particularly heavy feeds is accomplished while retaining good catalyst stability.

What is claimed is:

1. A catalyst comprising a matrix and at least one zeolite with structure type NES at least partially in its acid form and comprising silicon and at least one element T selected from the group consisting of aluminum iron, gallium and boron, said catalyst further comprising at least one metal which is deposited on said matrix and zeolite wherein said at least one metal is selected from the group comprising of metals from groups VIIB and VIB of the periodic table, and wherein said catalyst further comprises at least one metal selected from the group consisting of metals from groups IIIA and IVA of the periodic table.

2. A catalyst according to claim 1, characterized in that element T has been extracted from the zeolite with structure type NES and in that the overall Si/T atomic ratio is more than 20.

3. A catalyst according to claim 1, in which the overall Si/T atomic ratio of the zeolite with structure type NES is in the range 25 to 350.

4. A catalyst according to claim 1, in which the zeolite with structure type NES is NU-87 zeolite.

5. A catalyst according to claim 4, in which the metal selected from the group consisting of metals from groups VIIB and VIB comprises rhenium.

6. A catalyst according to claim 5, further containing at least one metal selected from the group consisting of metals from groups IIIA and IVA of the periodic table.

7. A catalyst according to claim 5, further comprising at least one element selected from indium and tin.

8. A catalyst according to claim 7, comprising sulphur.

9. A catalyst according to claim 4, further comprising at least one element selected from indium and tin.

10. A catalyst according to claim 1, in which the sodium content is less than 0.1% by weight with respect to the total weight of zeolite with structure type NES.

11. A catalyst according to claim 1, in which the metal selected from the group consisting of metals from groups VIIB and VIB comprises rhenium.

12. A catalyst according to claim 11, further containing at least one metal selected from the group consisting of metals from groups and IVA of the periodic table.

13. A catalyst according to claim 11, further comprising at least one element selected from indium and tin.

14. A catalyst according to claim 1, further comprising at least one element selected from indium and tin.

15. A catalyst according to claim 1, comprising sulfur.

16. A catalyst according to claim 1, comprising, by weight with respect to the total weight, 30% to 90% of the zeolite with structure type NES and 0.01% to 5% by weight of at least one element selected from the group consisting of elements from groups VIIB and VIB and at least one matrix making up the complement to 100%.

17. A catalyst according to claim 1, further comprising 0.01% to 5% of at least one element from groups IIIA and IVA of the periodic table.

18. A catalyst according to claim 1, in which the macroscopic distribution coefficient of the metal selected from the group consisting of metals from groups VIIB and VIB is in the range 0.7 to 1.3.

19. A catalyst according to claim 1, wherein the catalyst has a bed crush strength of more than 0.7 MPa.

20. A catalyst according to claim 1, wherein said catalyst is prepared by removing element T from synthesized NES zeolite containing an organic template by direct acid attack.

21. A catalyst according to claim 20, wherein said catalyst is prepared by mixing the matrix and the zeolite with structure type NES, forming the mixture and introducing at leastg one metal selected from the group consisting of metals from groups VIIB and VIB.

22. A catalyst according to claim 1, wherein said catalyst is prepared by removing element T from synthesized NES zeolite containing an organic template by heat treatment and acid attack.

23. A catalyst according to claim 22, in which the heat treatment is carried out in the presence of steam.

24. A catalyst comprising at least one binder, at least one zeolite with structure type NES at least partially in its acid form and comprising silicon and at least one element T selected from the group consisting of aluminum, iron, gallium and boron, said catalyst further comprising at least one metal selected from the group consisting of iridium and metals from groups VIIB and VIB of the periodic table, and at least one metal selected from the group consisting of metals from groups IIIa and IVa of the periodic table.

25. A catalyst comprising a matrix and at least one zeolite with structure type NES at least partially in its acid form and comprising silicon and at least one element T selected from The group consisting of aluminum iron, gallium and boron, said catalyst further comprising at least one metal which is deposited on said matrix and zeolite wherein said at least one metal is selected from the group consisting of metals from groups VIIB and VIB of the periodic table, and wherein said catalyst further comprises at least one element selected from indium and tin.

26. A catalyst comprising a matrix and at least one zeolite with structure type NES at least partially in its acid form and comprising silicon and at least one element T selected from the group consisting of aluminum iron, gallium and boron, said catalyst further comprising at least one metal which is deposited on said matrix and zeolite wherein said at least one metal is selected from the group consisting of metals from groups VIIB and VIB of the periodic table, and wherein said catalyst further comprises 0.01% to 5% of at least one element from groups IIIA and IVA of the periodic table.

* * * * *

UNITED STATES PATENT AND TRADEMARK OFFICE
CERTIFICATE OF CORRECTION

PATENT NO. : 6,613,709 B1
DATED : September 2, 2003
INVENTOR(S) : Elisabeth Merlen et al.

It is certified that error appears in the above-identified patent and that said Letters Patent is hereby corrected as shown below:

Title page,
Item [73], Assignee, "Cedex" should read -- Rueil-Mailmaison Cedex --.

Column 10,
Line 49, "groups and" should read -- groups IIIA and --.

Column 11,
Line 9, "leastg" should read -- least --.

Column 12,
Line 2, "groups IIIa and IVa" should read -- groups IIIA and IVA --.
Line 6, "The group" should read -- the group --.
Lines 6 and 15, "aluminum iron," should read -- aluminum, iron, --.

Signed and Sealed this

Twenty-sixth Day of April, 2005

JON W. DUDAS
*Director of the United States Patent and Trademark Office*